United States Patent
Tezuka (10) Patent No.: US 7,679,731 B2
(45) Date of Patent: Mar. 16, 2010

(54) DETECTING AND CHARACTERIZING MASK BLANK DEFECTS USING ANGULAR DISTRIBUTION OF SCATTERED LIGHT

(75) Inventor: Yoshihiro Tezuka, Tsukuba (JP)

(73) Assignee: Intel Corporation, Santa Clara, CA (US)

(*) Notice: Subject to any disclaimer, the term of this patent is extended or adjusted under 35 U.S.C. 154(b) by 316 days.

(21) Appl. No.: 11/323,258

(22) Filed: Dec. 30, 2005

(65) Prior Publication Data

US 2007/0158636 A1 Jul. 12, 2007

(30) Foreign Application Priority Data

Dec. 22, 2005 (JP) ............... 2005-370205

(51) Int. Cl.
*G01N 21/00* (2006.01)
(52) U.S. Cl. ..................... 356/72
(58) Field of Classification Search .... 356/237.1–237.3
See application file for complete search history.

(56) References Cited

U.S. PATENT DOCUMENTS

| | | | | |
|---|---|---|---|---|
| 3,076,378 A * | 2/1963 | Biedermann et al. ......... 355/68 |
| 4,076,420 A * | 2/1978 | De Maeyer et al. .......... 356/73 |
| 4,598,981 A * | 7/1986 | Hallam et al. ............... 359/366 |
| 5,131,023 A * | 7/1992 | Yasugaki et al. ............. 378/43 |
| 5,144,477 A * | 9/1992 | White ........................ 359/368 |
| 5,291,339 A * | 3/1994 | Mochimaru et al. ......... 359/859 |
| 5,808,312 A * | 9/1998 | Fukuda ..................... 250/492.2 |
| 6,162,577 A * | 12/2000 | Felter et al. ................ 430/270.1 |
| 6,522,717 B1 * | 2/2003 | Murakami et al. ........... 378/43 |
| 6,954,266 B2 * | 10/2005 | Tomie ....................... 356/237.1 |
| 2005/0093041 A1 * | 5/2005 | Singer et al. ................ 257/295 |

FOREIGN PATENT DOCUMENTS

JP 2004-193269 7/2004

OTHER PUBLICATIONS

Yoshihiro Tezuka, "Actinic detection of multilayer defects on EUV mask blanks using LPP light source and dark-field imaging", Proceedings of SPIE, vol. 5374, pp. 271-280, 2004.

* cited by examiner

*Primary Examiner*—Tarifur R. Chowdhury
*Assistant Examiner*—Isiaka O Akanbi
(74) *Attorney, Agent, or Firm*—Blakely, Sokoloff, Taylor & Zafman LLP (57) ABSTRACT

An embodiment of the present invention is a technique to inspect defects in mask blanks. A first iris diaphragm is located at an illumination source to limit an illumination angle of light emitted from the illumination source. A scattering limit unit is located at exit of a dark field optical unit to limit scattering angle of the light scattered after reflecting from a mask blank. A defect analyzer is optically coupled to the dark field optical unit to generate an angular distribution of the scattered light. The angular distribution is used to characterize criticality of a defect found on the mask blank.

27 Claims, 8 Drawing Sheets

DETECTING AND CHARACTERIZING MASK BLANK DEFECTS USING ANGULAR DISTRIBUTION OF SCATTERED LIGHT

RELATED APPLICATION

This patent application claims the benefits of the Japanese patent application, filed on Dec. 22, 2005, Application No. 2005-370205.

BACKGROUND

1. Field of the Invention

Embodiments of the invention relate to the field of semiconductor fabrication, and more specifically, to mask blank inspection.

2. Description of Related Art

Extreme Ultraviolet Lithography (EUVL) has become a preferred technique for optical lithography. EUVL typically uses a reflective mask architecture. A defect on the mask may cause defective image of the pattern on the wafer. Therefore, mask blank inspection is necessary to provide qualification of each mask blank before and after shipment to users. Defects in mask blanks need to be analyzed to determine defect criticality.

Existing techniques to address the above problem have a number of drawbacks In actinic inspection, extreme ultraviolet (EUV) radiation is used together with dark field imaging and two-dimensional image sensors. This method may provide sensitive inspection for multilayer defect detection in EUV mask blanks. However, this method relies only on the inspection signal intensity. This is insufficient to decide whether the detected defect is critical or not. Another method uses EUV microscope with large magnification to resolve uncertainty in criticality. However, its effectiveness is not demonstrated. In addition, using an EUV microscope with high magnification is expensive.

BRIEF DESCRIPTION OF THE DRAWINGS

Embodiments of invention may best be understood by referring to the following description and accompanying drawings that are used to illustrate embodiments of the invention. In the drawings.

DESCRIPTION

An embodiment of the present invention is a technique to inspect defects in mask blanks. A first iris diaphragm is located at an illumination source to limit an illumination angle of light emitted from the illumination source. A scattering limit unit is located at exit of a dark field optical unit to limit scattering angle of the light scattered after reflecting from a mask blank. A defect analyzer is optically coupled to the dark field optical unit to generate an angular distribution of the scattered light. The angular distribution is used to characterize criticality of a defect found on the mask blank In the following description, numerous specific details are set forth. However, it is understood that embodiments of the invention may be practiced without these specific details. In other instances, well-known circuits, structures, and techniques have not been shown to avoid obscuring the understanding of this description.

One embodiment of the invention may be described as a process which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a program, a procedure, a method of manufacturing or fabrication, etc.

One embodiment of the invention provides a characterization of defect criticality using angular distribution curves and risk level data. The defect characterization information may be used to minimize risk of generating printable defects during pattern writing. The technique involves two modes of operation: a detection mode and a characterization mode. In the detection mode, the defects are located by examining the whole area on the mask blank. In the characterization mode, the detected defect is further examined to obtain the images at various limiting angles. The images are then converted into an intensity function with respect to the angles. The result is an angular distribution curve for the scattered light. This angular distribution curve is then compared with information in a database to provide criticality measurement and risk level for each defect. The criticality measurement and risk level are used during pattern writing procedure to minimize the risk of generating printable defects.

Figure 1:
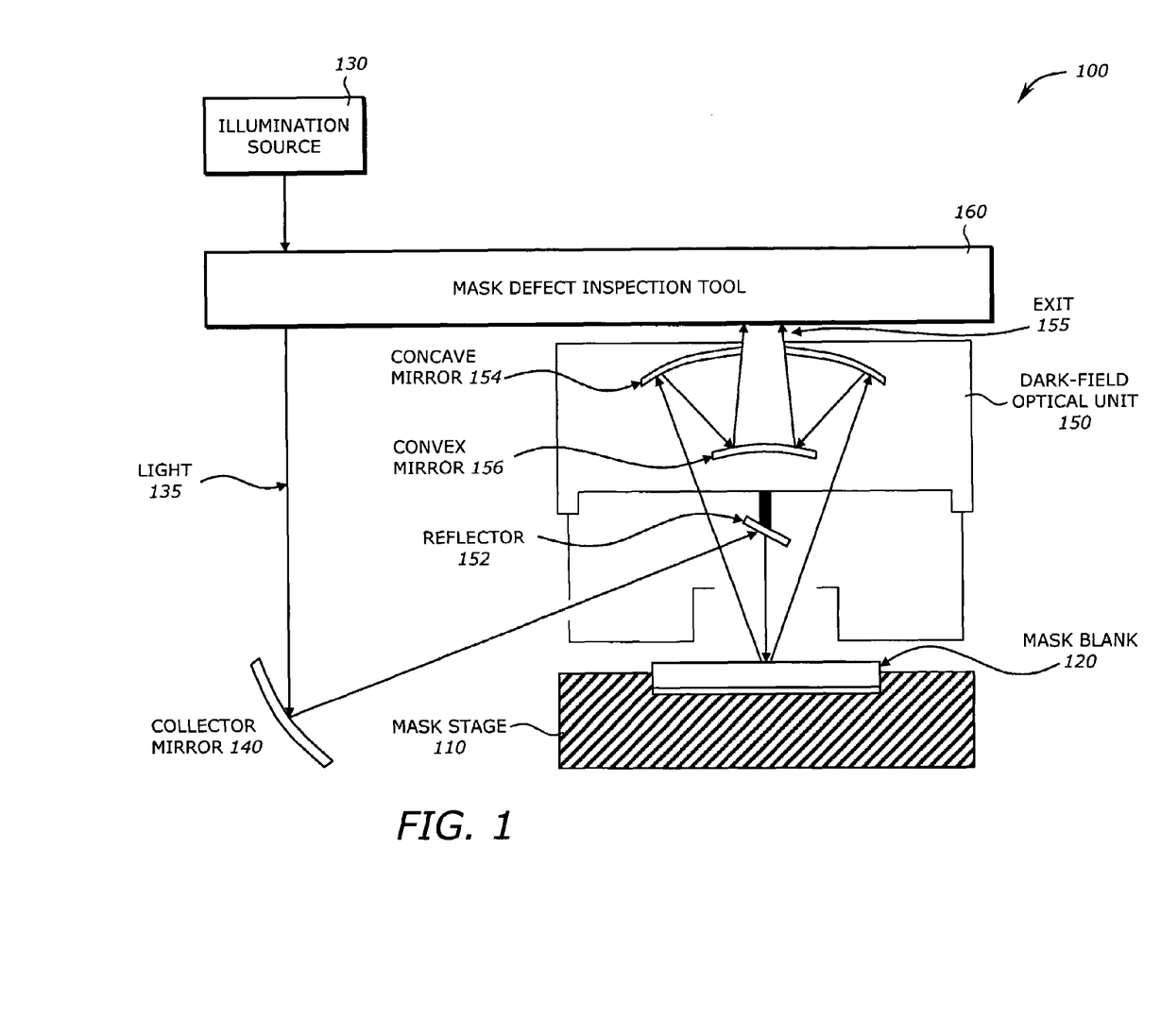
FIG. 1 is a diagram illustrating a system in which one embodiment of the invention can be practiced.

FIG. 1 is a diagram illustrating a system 100 in which one embodiment of the invention can be practiced. The system 100 represents an extreme ultraviolet (EUV) exposure system to inspect defects in mask blank. The system 100 includes a mask stage 110, a mask blank 120, an illumination source 130, a collector mirror 140, a dark-field optical unit 150, and a mask defect inspection tool 160. The system 100 may contain more or less than the above elements.

The mask stage 110 secures and holds the mask blank 120 during the inspection. The mask stage 110 may have stepping or movement mechanism that moves, rotates, or steps the mask blank 120 for accurate positioning and/or alignment. It may support the mask blank 120 via a reticle chuck (not shown). The position of the mask stage 110 and the mask blank 120 may be monitored by a laser interferometer (not shown). The mask blank 120 may be a multilayer coated reflective mask. It may include multiple layers of alternating molybdenum (Mo), amorphous silicon (Si), or beryllium (Be) deposited on a super-polished substrate. The mask blank 120 may have defects caused by defects in the coating. The defects in the mask blank 120 may change the reflected field of the light during pattern writing, leading to defects in the pattern printing on the wafer. It is, therefore, important to inspect the mask blanks before using in pattern writing process. Traditional inspection techniques such as using high power microscope may not characterize the defects in a useful manner. The defect criticality may not be determined.

The illumination source 130 may be a laser-plasma source, a discharge plasma source, or a synchrotron radiation source to generate a beam of EUV light 135. The laser plasma light source may irradiate a highly intensified pulse laser beam to a target material in vacuum, and generates high-temperature plasma for use as EUV light with a wavelength of about 13.4 nm. The EUV light beam 135 goes through the mask defect inspection tool 160 to the collector mirror 140 and reflects to the dark-field optical unit 150. The dark-field optical unit 150 provides dark-field observation of the image formed by scattered light as the light beam 135 is deflected onto the mask blank 120. In one embodiment, the dark-field optical unit 150 is a Schwarzschild optical system. The dark field optical unit 150 includes a reflector 152, a concave mirror 154, and a convex mirror 156. The reflector 152 deflects the EUV light beam 135 onto the mask blank 120. The mask blank 120 reflects the light to the concave mirror 154 which in turns reflects light to the convex mirror 156. The light is scattered through an exit 155 to the mask defect inspection tool 160.

The mask defect inspection tool 160 is optically coupled with the illumination source 130 and the dark-field optical unit 150 to provide a means to characterize the criticality of defects detected in the mask blank 120. It may resolve uncertainty in defect characterization. The characterized defect criticality may be converted into defect risk levels and used as part of the defect data of a particular mask blank. The defect data may be used during the pattern writing process to minimize the risk of generating printable defects on the semiconductor wafer.

Figure 2A:
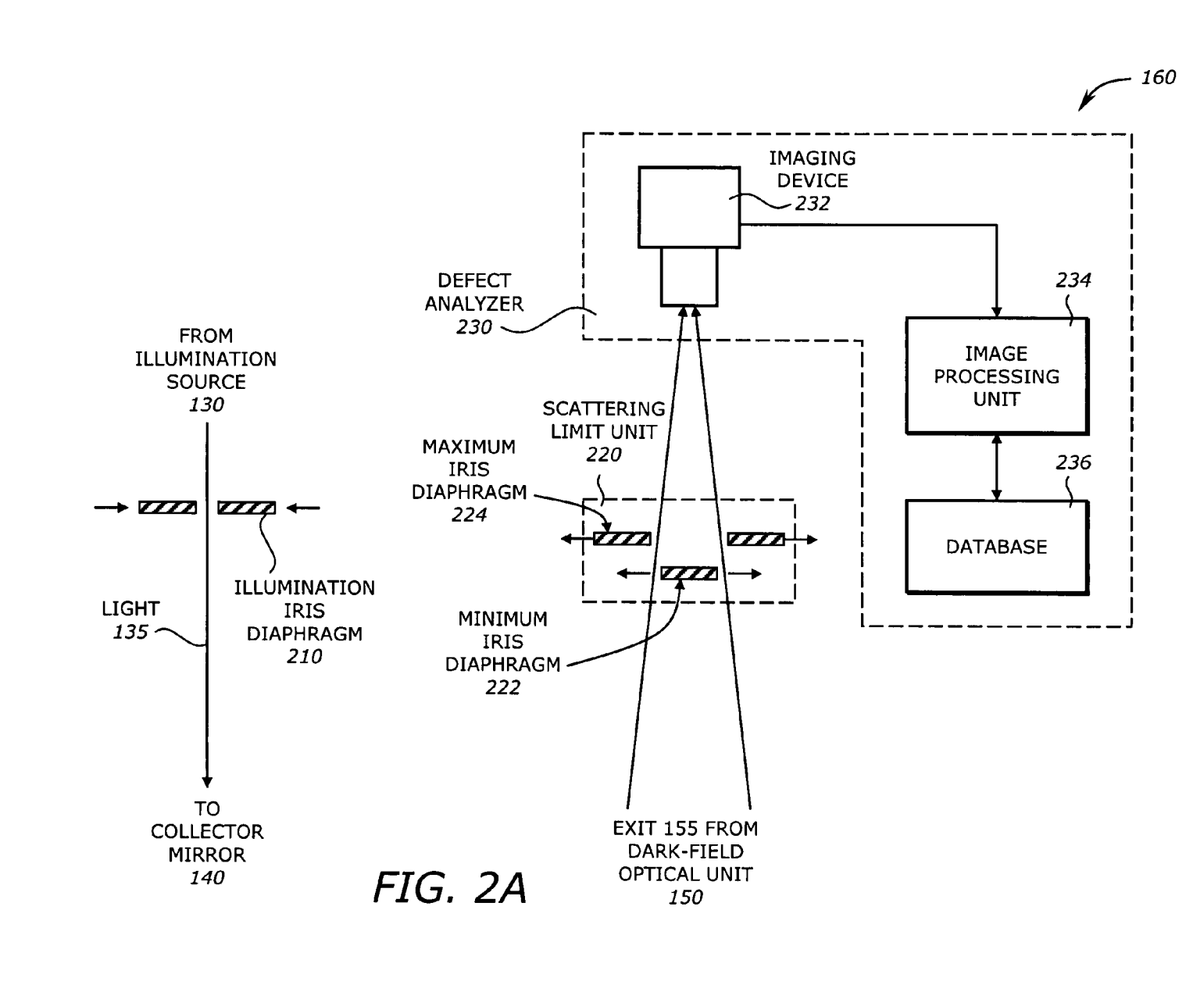
FIG. 2A is a diagram illustrating a mask defect inspection tool according to one embodiment of the invention.

FIG. 2 is a diagram illustrating the mask defect inspection tool 160 shown in FIG. 1 according to one embodiment of the invention. The mask defect inspection tool 160 includes an illumination iris diaphragm 210, a scattering limit unit 220, and a defect analyzer 230.

The illumination iris diaphragm 210 is located at the illumination source 130 to limit an illumination angle of the light 135 emitted from the illumination source 130. It is a diaphragm having an adjustable aperture. The aperture may be controlled by the defect analyzer 230 or manually. The illumination iris diaphragm 210 may be used in both detection and characterization modes.

The scattering limit unit 220 is located at the exit 135 of the dark field optical unit 150 to limit scattering angle of the light scattered after reflecting from the mask blank 120. The scattering limit unit 220 may include a minimum iris diaphragm 222 and a maximum iris diaphragm 224. These iris diaphragms are referred to as imaging iris diaphragms because they are located at the exit of the dark-field optical unit 150 to provide image to be captured by the mask defection inspection tool 160. The minimum iris diaphragm 222 limits a minimum scattering angle of the scattered light. The maximum iris diaphragm 224 limits a maximum scattering angle of the scattered light. In one embodiment, only one of the two iris diaphragms 222 and 224 is used. When only one of the two iris diaphragms 222 and 224 is used, it may be set at two limit scattering angles to provide difference image data. The range of the angles may be from 0 to 30 degrees with a typical range from 6-18 degrees.

The defect analyzer 230 is optically coupled to the dark field optical unit 150 to generate an angular distribution of the scattered light. The angular distribution is used to characterize criticality of a defect found on the mask blank 120. The defect analyzer 230 includes an imaging device 232, a processing unit 234, and a database 236.

The imaging device 232 obtains an image of the scattered light. It may be a charge coupled device (CCD) camera with sufficiently high resolution. It may also have a built-in image digitizer to digitize the image and provide the digital image to the image processing unit 234. Alternatively, the image digitization may be performed by the image processing unit 234.

The image processing unit 234 receives the image captured by the imaging device and processes the image to provide the angular distribution. The processing unit 234 may also control the illumination iris diaphragm 210 and/or the scattering limit unit 220. There are a number of ways to generate the angular distribution data from a defect image. In one method, the defect intensity is expressed as a one-dimensional function of the scattering angle. In this method, the illumination iris diaphragm 210 is first set at a pre-determined angle. For example, the angle may be a few degrees. Then, one or both of the minimum and maximum iris diaphragms 222 and 224 is or are set at the starting angle. The imaging device 232 then takes an image of the scattered light. One of the minimum and maximum iris diaphragms 222 and 224 is then updated, either by incrementing if the starting angle is the minimum angle of the range or decrementing if the starting angle is the maximum angle of the range. Each time the minimum or maximum iris diaphragm 222 or 224 is updated, the imaging device 232 obtains the image of the scattered light until the ending angle is reached. The processing unit 234 converts the image intensity at each angle into a defect intensity value at that angle. This may be performed by integrating the pixel intensity of the pixels surrounding the defect center. The window if integration may have some pre-determined size (e.g., 7×7, 9×9, or 11×11). The background intensity of the area without defect is then subtracted from this integrated defect intensity. A normalization procedure may be applied to the resulting intensity. This computation is repeated for all the angles in the range. The result is a one dimensional angular distribution curve which is a function of the defect size with respect to the angle.

The database 236 stores a set of defect parameters obtained analytically or experimentally. The set of defect parameters is compared with the angular distribution to provide a risk level for the defect. The defect parameters may include the height, width, or volume of the defect and the associated angular distribution data. The risk level may be expressed as a number which represents a combination of the defect parameters. For example, if the angular distribution curve shows large fluctuations over the angular range and the defect size is large, the risk level may be determined as high. If the angular distribution curve is relative smooth or flat and the defect size is small, the risk level may be determined as low.

Figure 2B:
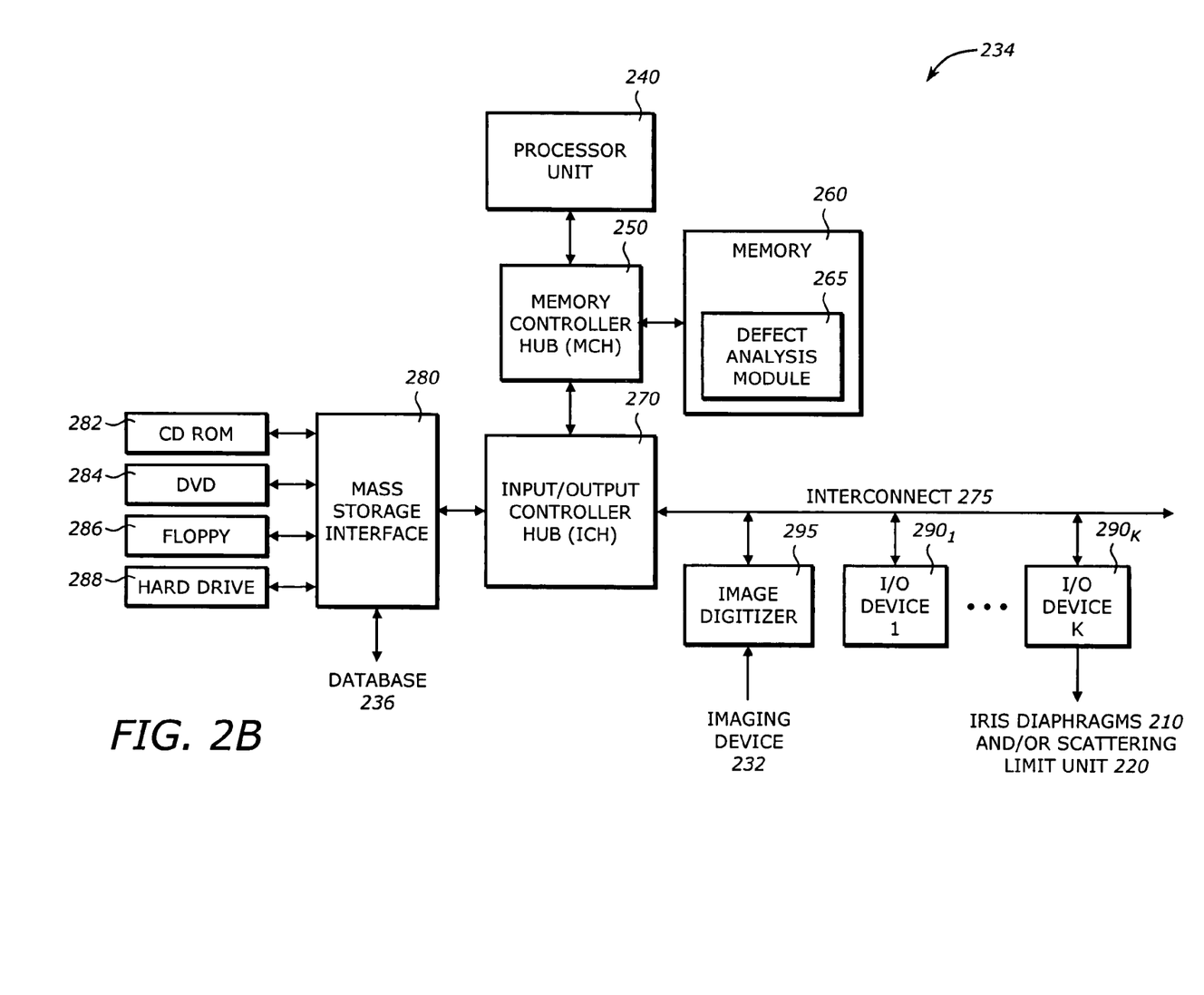
FIG. 2B is a diagram illustrating an image processing unit according to one embodiment of the invention.

FIG. 2B is a diagram illustrating the image processing unit 234 shown in FIG. 2A according to one embodiment of the invention. The image processing unit 234 includes a processor unit 240, a memory controller hub (MCH) 250, a main memory 260, an input/output controller hub (IOH) 270, an interconnect 275, a mass storage interface 280, input/output (I/O) devices $290_1$ to $290_K$, and an image digitizer 295.

The processor unit 240 represents a central processing unit of any type of architecture, such as processors using hyper threading, security, network, digital media technologies, single-core processors, multi-core processors, embedded processors, mobile processors, micro-controllers, digital signal processors, superscalar computers, vector processors, single instruction multiple data (SIMD) computers, complex instruction set computers (CISC), reduced instruction set computers (RISC), very long instruction word (VLIW), or hybrid architecture.

The MCH 250 provides control and configuration of memory and input/output devices such as the main memory 260 and the ICH 270. The MCH 250 may be integrated into a chipset that integrates multiple functionalities such as graphics, media, isolated execution mode, host-to-peripheral bus interface, memory control, power management, etc. The MCH 250 or the memory controller functionality in the MCH 250 may be integrated in the processor unit 240. In some embodiments, the memory controller, either internal or external to the processor unit 240, may work for all cores or processors in the processor unit 240. In other embodiments, it may include different portions that may work separately for different cores or processors in the processor unit 240.

The main memory 260 stores system code and data. The main memory 260 is typically implemented with dynamic random access memory (DRAM), static random access memory (SRAM), or any other types of memories including those that do not need to be refreshed. The main memory 260 may include multiple channels of memory devices such as DRAMs. The DRAMs may be Double Data Rate (DDR2). The main memory may contain a defect analysis module 265 to perform the defect analysis tasks as described below.

The ICH 270 has a number of functionalities that are designed to support I/O functions. The ICH 270 may also be integrated into a chipset together or separate from the MCH 250 to perform I/O functions. The ICH 270 may include a number of interface and I/O functions such as peripheral component interconnect (PCI) bus interface, processor interface, interrupt controller, direct memory access (DMA) controller, power management logic, timer, system management bus (SMBus), universal serial bus (USB) interface, mass storage interface, low pin count (LPC) interface, etc.

The interconnect 275 provides interface to peripheral devices. The interconnect 275 may be point-to-point or connected to multiple devices. For clarity, not all of the interconnects are shown. It is contemplated that the interconnect 275 may include any interconnect or bus such as Peripheral Component Interconnect (PCI), PCI Express, Universal Serial Bus (USB), and Direct Media Interface (DMI), etc.

The mass storage interface 280 provides interface to a mass storage device to store archive information such as code, programs, files, data, and applications. The mass storage device may include a compact disk (CD) read-only memory (ROM) 282, a digital video/versatile disc (DVD) 284, a floppy drive 286, and a hard drive 288, and any other magnetic or optic storage devices. The mass storage device provides a mechanism to read machine-accessible media. The database 236 may be stored in any of these mass storage devices or interfaced directly to the mass storage interface 280. The I/O devices $290_1$ to $290_K$ may include any I/O devices to perform I/O functions including the control of the illumination iris diaphragm 210 and/or the scattering limit unit 220. Examples of I/O devices $290_1$ to $290_K$ include controller for input devices (e.g., keyboard, mouse, trackball, pointing device), media card (e.g., audio, video, or graphic), network card, and any other peripheral controllers. The image digitizer 295 digitizes the image or video signal from the imaging device 232. It may be optional if the imaging device 232 has its own digitizer.

Figure 3A:
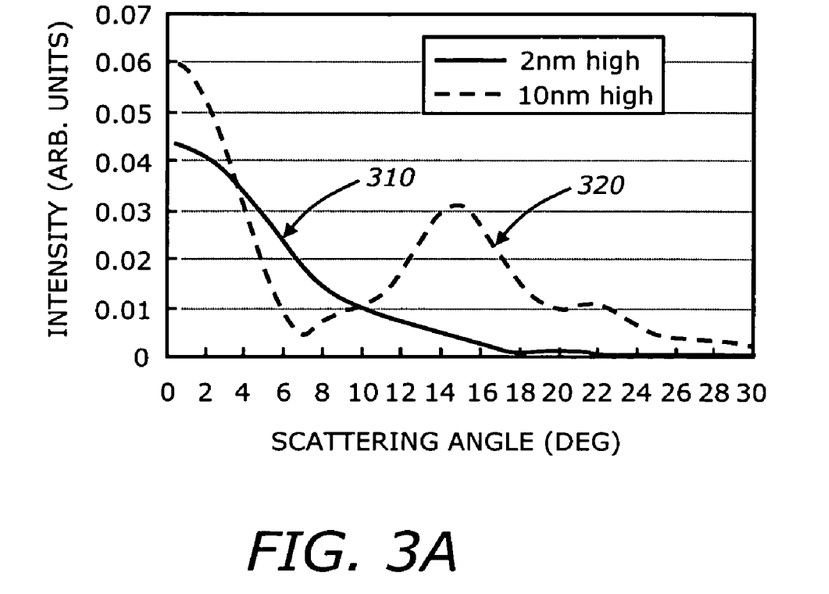
FIG. 3A is a diagram illustrating a first example of angular distribution curves according to one embodiment of the invention.

FIG. 3A is a diagram illustrating a first example of angular distribution curves according to one embodiment of the invention. In this first example, there are two detected defects, both having a width of 60 nanometers (nm). The first defect has a height of 2 nm and an angular distribution curve 310. The second defect has a height of 10 nm and an angular distribution curve 320.

Both of the angular distribution curves 310 and 320 show the intensity level in some normalized intensity unit as function of the scattering angle ranging from 0 degree to 30 degrees. The angular distribution curve 310 is a smooth curve having a Gaussian shape. The angular distribution curve 320 shows a strong dip in the range of 6 to 10 degrees. The average intensities of the two defects are similar. Therefore, if only average intensity is used to characterize the criticality level of the defects, both defects may be judged as similar. However, if the angular distribution curves are examined and compared, the second defect has higher risk of defect printing because its angular distribution curve 320 has a stronger valley at 6-10 degrees and a stronger peak at 14-16 degrees.

Figure 3B:
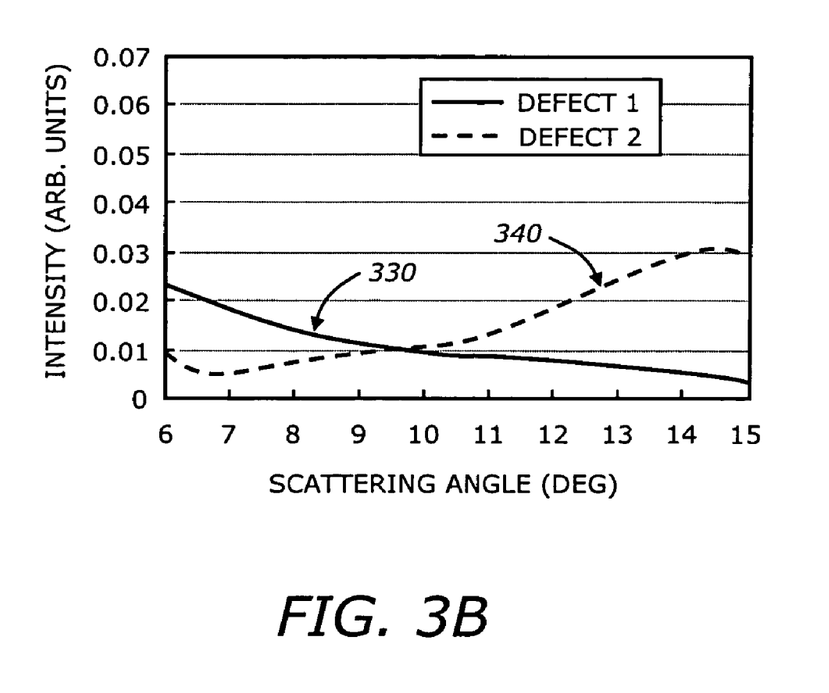
FIG. 3B is a diagram illustrating a second example of angular distribution curves according to one embodiment of the invention.

FIG. 3B is a diagram illustrating a second example of angular distribution curves according to one embodiment of the invention. In this second example, there are two angular distribution curves 330 and 340 corresponding to a first defect and a second defect, respectively. Both angular distribution curves are obtained using the optics having numerical aperture (NA) of 0.25. The average intensities of these two defects are approximately the same. Therefore, if only signal intensity is used, both defects may be judged as similar. However, examining and comparing the two angular distribution curves show that the second defect is more critical and has a higher risk.

The angular distribution curve 330 has a smoother characteristic. The downtrend portion of the curve 330 suggests a small defect and low risk. On the contrary, the angular distribution curve 340 has a stronger intensity uptrend in the angle range between 6 and 15 degrees. The uptrend portion of the curve 340 suggests a large defect and high risk. Therefore, the second defect indicates a larger defect with higher risk.

Figure 4:
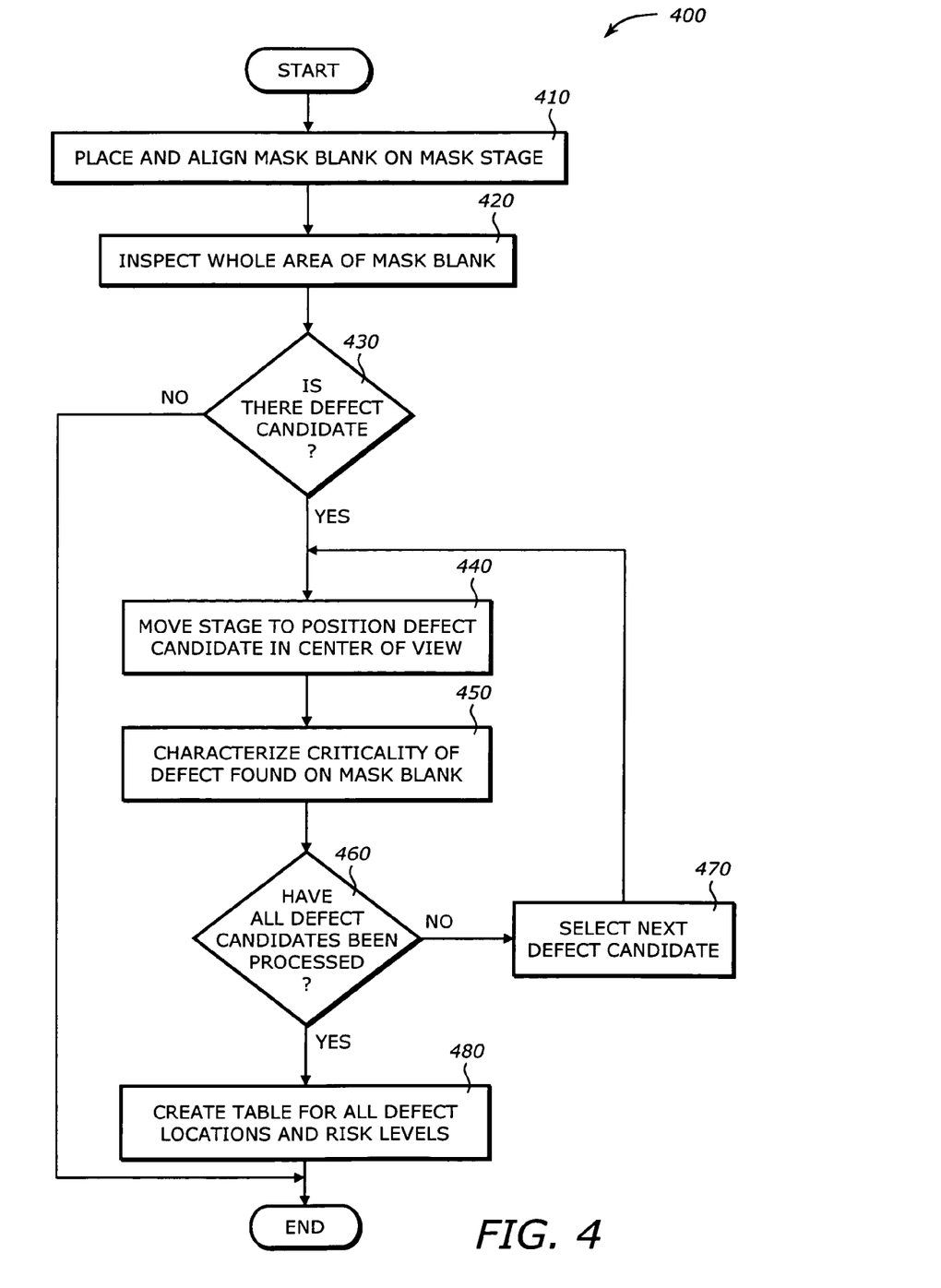
FIG. 4 is a flowchart illustrating a process to inspect mask defects according to one embodiment of the invention.

FIG. 4 is a flowchart illustrating a process 400 to inspect mask defects according to one embodiment of the invention. The process 400 may be performed manually, automatically, or both manually and automatically.

Upon START, the process 400 places and aligns a mask blank on the mask stage (Block 410). Then, the process 400 inspects the whole area of the mask blank (Block 420). Next, the process 400 determines if there is a defect candidate on the mask blank (Block 430). If not, the process 400 is terminated. Otherwise, the process 400 moves the mask stage to position the defect candidate in center of view of the imaging device (Block 440). This allows the imaging device to obtain a better image of the defect candidate.

Then, the process 400 characterizes the criticality of the defect candidate found on the mask blank (Block 450). The criticality may be represented by an angular distribution curve. Next, the process 400 determines if all the defect candidates have been processed (Block 460). If not, the process 400 selects the next defect candidate (Block 470) and returns to Block 440 to continue the inspection process. Otherwise, the process 400 creates a table for all the defect locations and the risk levels as obtained from the criticality characteristics (Block 480). The table may be in any suitable format for comparison. The process 400 is then terminated.

Figure 5:
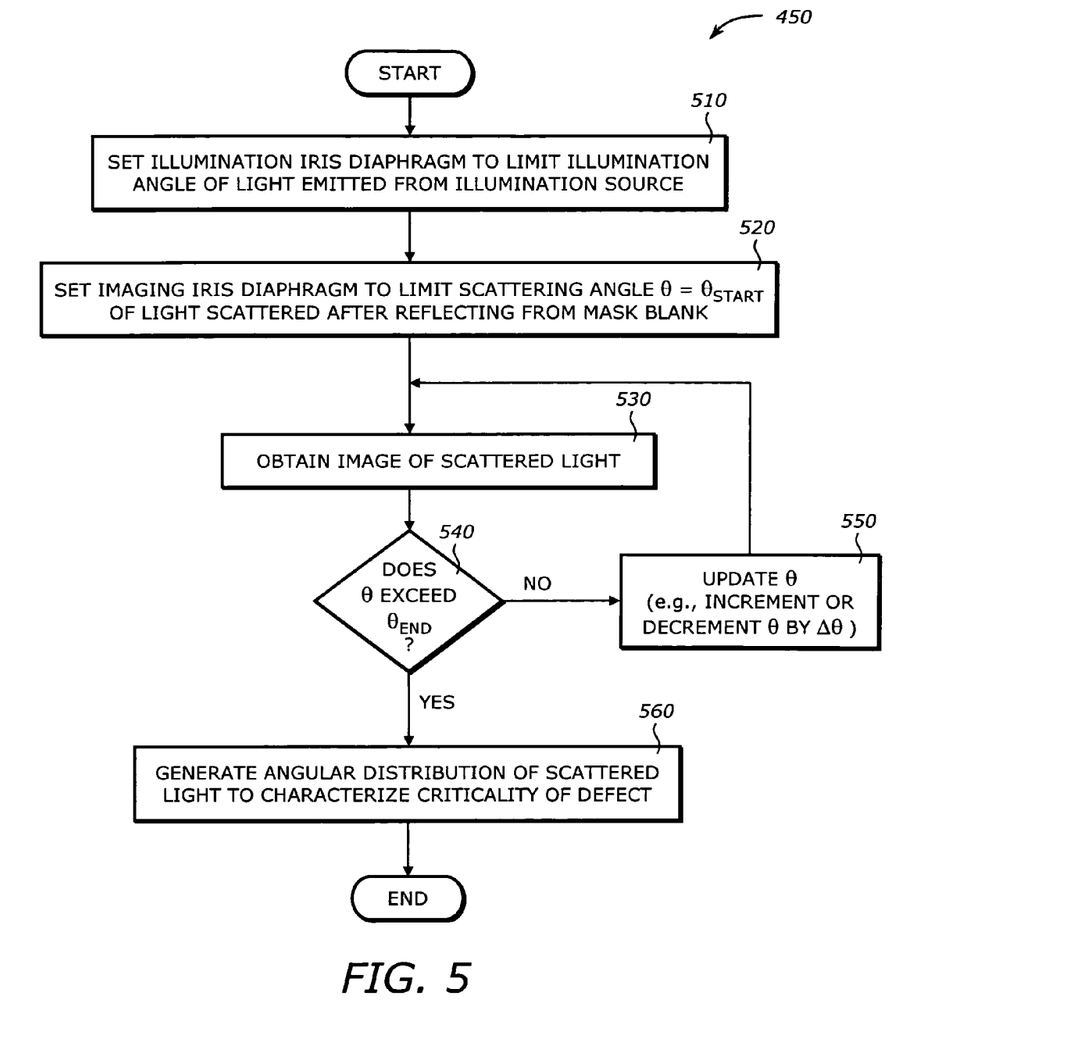
FIG. 5 is a flowchart illustrating a process to characterize defect criticality according to one embodiment of the invention.

FIG. 5 is a flowchart illustrating the process 450 shown in FIG. 4 to characterize the defect criticality according to one embodiment of the invention.

Upon START, the process 450 sets the illumination iris diaphragm to limit the illumination angle of light emitted from the illumination source (Block 510). Typically the limit illumination angle is a few degrees or less. Next, the process 450 sets the imaging iris diaphragm or diaphragms to limit the scattering angle θ of the light scattered from the dark-field optical unit after reflecting from the mask blank (Block 520). The process 450 sets the angle to a pre-determined start limit angle $θ_{start}$. The angular distribution curve may be obtained for an angle ranging from $θ_{start}$ to $θ_{end}$.

Next, the process 450 obtains the image of the scattered light (Block 530). This image represents the defect being examined. Then, the process 450 determines if the limit scattering angle θ exceeds a predetermined ending angle $θ_{end}$ (Block 540). If not, the process 450 updates the limit scattering angle θ to a new value, such as decrementing or incrementing the angle θ by an angular increment Δθ (Block 550) and returns to Block 530 to continue the imaging of the defect. The angular increment Δθ may be less than a few degrees. If the limit angle θ exceeds the ending angle $θ_{end}$, the process 450 generates an angular distribution of the scattered light to characterize the criticality of the defect (Block 560) and is then terminated. The angular distribution may be represented by a curve showing the intensity of the defect over a range of the limit angle θ from $θ_{start}$ to $θ_{end}$.

One of the iris diaphragms in the imaging path may be used to generate a difference image that may provide the angular distribution curve. For example, the maximum iris diaphragm 224 may be used first to set the angle to $θ_1$. A first image is then taken at this angle setting. Then, it is set at $θ_2<θ_1$, and a second image is taken at this angle setting. The difference image of the two images is in essence equivalent to an image taken with a lower setting of $θ_2$ and a higher setting of $θ_1$.

Figure 6:
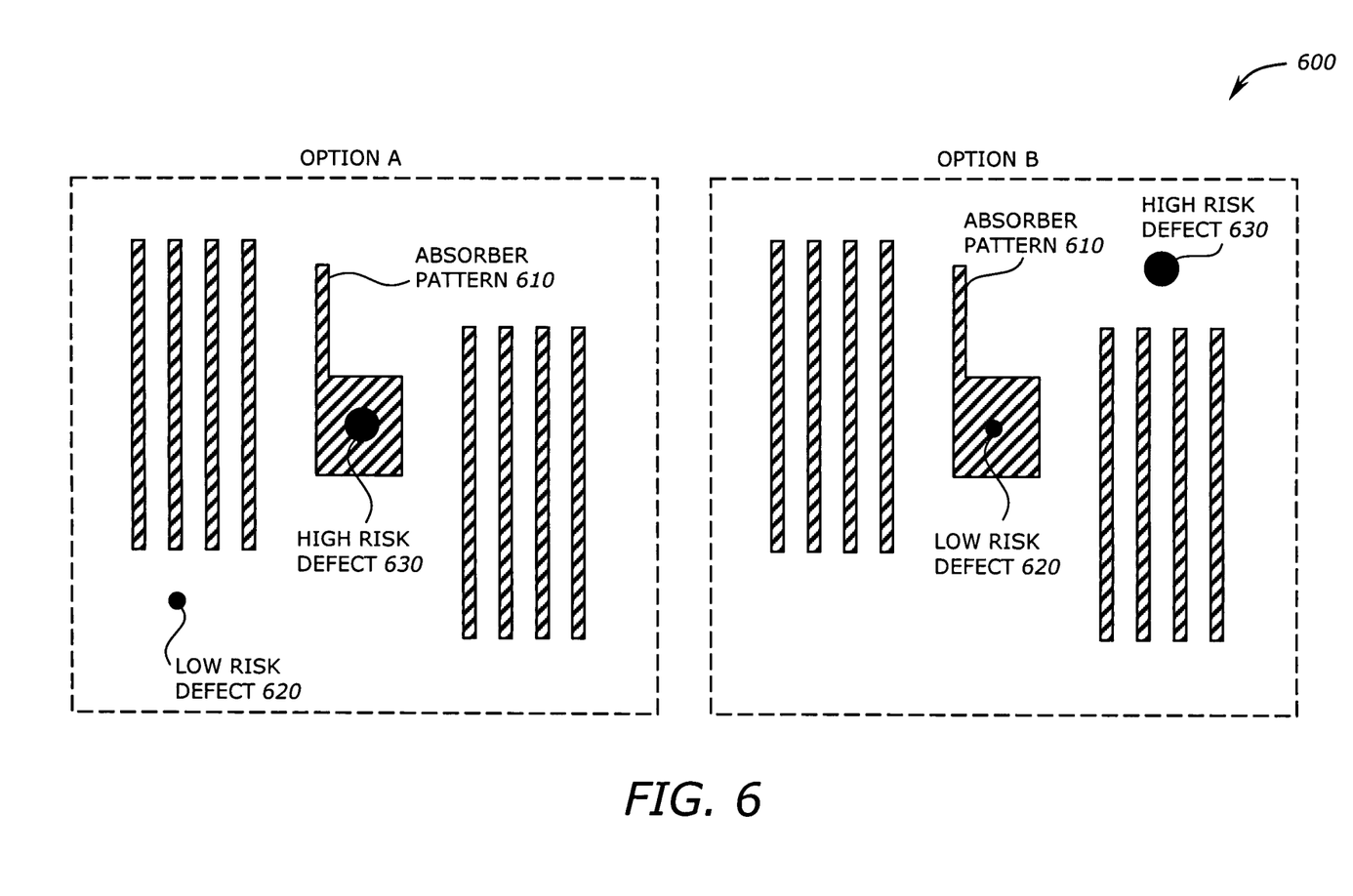
FIG. 6 is a diagram illustrating an example of mask pattern placement options according to one embodiment of the invention.

FIG. 6 is a diagram illustrating an example of mask pattern placement options according to one embodiment of the invention. There are two options: option A and option B. The mask pattern placement includes an absorber pattern 610, a relatively low risk defect 620, and a relatively high risk defect 630.

In option A, the high risk defect 630 is underneath the absorber pattern 610 and the low risk defect 620 is exposed. In option B, the low risk 620 is underneath the absorber pattern 610 and the high risk defect 630 is exposed. When a defect is below a large absorber pattern, it has little impact to reflectivity because the absorber itself literally absorbs the EUV light regardless of what is lying underneath. Therefore, option A is preferred to option B because the impact of the high risk defect 630 is minimized by virtue of its being underneath the absorber pattern 610. On the contrary, in option B, the high risk defect 630 is exposed to therefore may cause larger printable defect.

Figure 7:
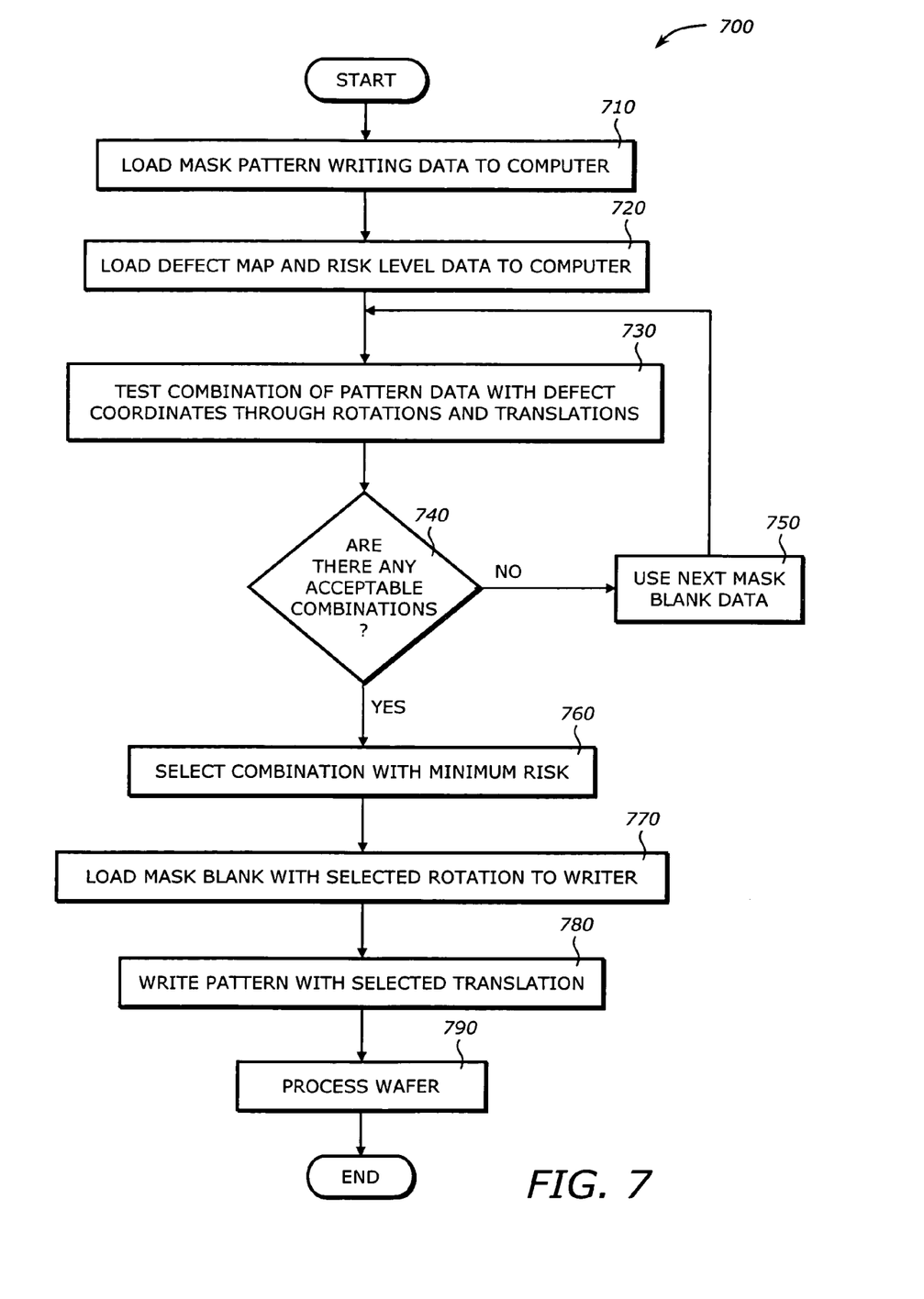
FIG. 7 is a flowchart illustrating a process to write mask pattern according to one embodiment of the invention.

FIG. 7 is a flowchart illustrating a process 700 to write mask pattern according to one embodiment of the invention. The process 700 is normally performed after the criticality information and the risk level for all defects in the mask blank have been obtained as discussed above.

Upon START, the process 700 loads the mask pattern writing data to the computer or a processing unit (Block 710). Next, the process 700 loads the defect map and risk level data to the computer or the processing unit (Block 720). Then, the process 700 tests all combinations of pattern data with defect coordinates through rotations and translations (Block 730). There are typically four rotations: 0, 90, 180, and 270 degrees. There are two translations: x direction and y direction. The increments for the translation depends on the die size. For example, if the die size is 100 mm×100 mm, then the translation may be +/−6 mm in the x-direction and +/−16 mm in the y-direction.

Next, the process 700 determines if there are any acceptable or allowable combinations (Block 740). If not, the process 700 uses the next mask blank data from the loaded defect map and risk level data (Block 750). Otherwise, the process 700 selects the combination that provides the minimum risk (Block 760).

Then, the process 700 loads the mask blank with the selected rotation to the writer (Block 770). Next, the process 700 writes the pattern with the selected translation (Block 780). Then, the process 700 proceeds with the processing of the wafer (Block 790). The wafer processing may include operations such as resist development, etching, etc. The process 700 is then terminated.

The process of generating the angular distribution curves or providing the risk level or any other criticality measure may be performed manually or automatically. Once the database is constructed, the process of selecting the best combination for pattern writing may be automated.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting.

What is claimed is:

1. An apparatus comprising:
   a first iris diaphragm located at an illumination source to limit an illumination angle of light emitted from the illumination source to a dark field optical unit;
   a scattering limit unit located at exit of the dark field optical unit to limit scattering angle of the light scattered after reflecting from a mask blank; and
   a defect analyzer optically coupled to the dark field optical unit to generate an angular distribution of the scattered light, the angular distribution being used to characterize criticality of a defect found on the mask blank;
   wherein the scattering limit unit comprises:
   a second iris diaphragm to limit a minimum scattering angle of the scattered light.

2. The apparatus of claim 1 wherein the scattering limit unit comprises:
   a third iris diaphragm to limit a maximum scattering angle of the scattered light.

3. The apparatus of claim 2 wherein the defect analyzer comprises:
   an imaging device to obtain an image of the scattered light; and
   a processing unit coupled to the imaging device to process the image to provide the angular distribution.

4. The apparatus of claim 3 wherein the processing unit comprises:
   a database to store a set of defect parameters obtained analytically or experimentally, the set of defect parameters being compared with the angular distribution to provide a risk level for the defect.

5. The apparatus of claim 3 wherein the processing unit expresses defect density as a one-dimensional function of an incrementing or decrementing scattering angle.

6. The apparatus of claim 2 wherein the light is an extreme ultraviolet (EUV) light.

7. The apparatus of claim 2 wherein the dark-field optical unit is a Schwarzschild optical system.

8. The apparatus of claim 1 wherein the second iris diaphragm is set at two limit scattering angles to provide difference image data.

9. The apparatus of claim 8 wherein at least one of the two limit scattering angles ranges from 0 to 30 degrees.

10. A method comprising:
limiting an illumination angle of light emitted from an illumination source to a dark field optical unit by a first iris diaphragm located at the illumination source;
limiting scattering angle of the light scattered after reflecting from a mask blank by a scattering limit unit located at exit of the dark field optical unit; and
generating an angular distribution of the scattered light, the angular distribution being used to characterize criticality of a defect found on the mask blank;
wherein limiting scattering angle comprises:
limiting a minimum scattering angle of the scattered light by a second iris diaphragm.

11. The method of claim 10 wherein limiting scattering angle comprises:
limiting a maximum scattering angle of the scattered light by a third iris diaphragm.

12. The method of claim 11 wherein generating the angular distribution comprises:
obtaining an image of the scattered light; and
processing the image to provide the angular distribution.

13. The method of claim 12 wherein processing the image comprises:
comparing a set of defect parameters with the angular distribution to provide a risk level for the defect, the set of defect parameters being stored in a database and obtained analytically or experimentally.

14. The method of claim 12 wherein processing comprises expresses defect density as a one-dimensional function of an incrementing or decrementing scattering angle.

15. The method of claim 11 wherein limiting the illumination angle of the light comprises limiting the illumination angle of an extreme ultra violet (EUV) light.

16. The method of claim 10 wherein the dark-field optical unit is a Schwarzschild optical system.

17. The method of claim 10 wherein the second iris diaphragm is set at two limit scattering angles to provide difference image data.

18. The method of claim 17 wherein at least one of the two limit scattering angles ranges from 0 to 30 degrees.

19. A system comprising:
a mask stage to move a mask blank;
an illumination source to produce a light for inspecting the mask blank;
a dark field optical unit optically coupled to the illumination source to provide scattered light from the light deflected onto the mask blank; and
a defect inspection tool coupled to the illumination source and the dark field optical unit comprising:
a first iris diaphragm located at the illumination source to limit an illumination angle of the light emitted from the illumination source to the dark field optical unit,
a scattering limit unit located at exit of the dark field optical unit to limit scattering angle of the scattered light after reflecting from the mask blank, and
a defect analyzer optically coupled to the dark field optical unit to generate an angular distribution of the scattered light, the angular distribution being used to characterize criticality of a defect found on the mask blank;
wherein the scattering limit unit comprises:
a second iris diaphragm to limit a minimum scattering angle of the scattered light.

20. The system of claim 19 wherein the scattering limit unit comprises:
a third iris diaphragm to limit a maximum scattering angle of the scattered light.

21. The system of claim 20 wherein the defect analyzer comprises:
an imaging device to obtain an image of the scattered light; and
a processing unit coupled to the imaging device to process the image to provide the angular distribution.

22. The system of claim 21 wherein the processing unit comprises:
a database to store a set of defect parameters obtained analytically or experimentally, the set of defect parameters being compared with the angular distribution to provide a risk level for the defect.

23. The system of claim 21 wherein the processing unit expresses defect density as a one-dimensional function of an incrementing or decrementing scattering angle.

24. The system of claim 20 wherein the light is an extreme ultra violet (EUV) light.

25. The system of claim 19 wherein the dark-field optical unit is a Schwarzschild optical system.

26. The system of claim 19 wherein the second iris diaphragm is set at two limit scattering angles to provide difference image data.

27. The system of claim 26 wherein at least one of the two limit scattering angles ranges from 0 to 30 degrees.

* * * * *